United States Patent
Wang et al.

(10) Patent No.: US 9,168,327 B2
(45) Date of Patent: Oct. 27, 2015

(54) BONE/COLLAGEN COMPOSITES AND USES THEREOF

(75) Inventors: Sherry Hsiu-Ying Wang, North Brunswick, NJ (US); Michael Jaffe, Maplewood, NJ (US); Lawrence A. Shimp, Morganville, NJ (US); Nels J. Lauritzen, Piscataway, NJ (US); Charles M. Schiff, Yardley, PA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 818 days.

(21) Appl. No.: 12/744,810

(22) PCT Filed: Dec. 12, 2008

(86) PCT No.: PCT/US2008/086563
§ 371 (c)(1),
(2), (4) Date: May 26, 2010

(87) PCT Pub. No.: WO2009/076594
PCT Pub. Date: Jun. 18, 2009

(65) Prior Publication Data
US 2010/0256774 A1    Oct. 7, 2010

Related U.S. Application Data

(60) Provisional application No. 61/013,002, filed on Dec. 12, 2007.

(51) Int. Cl.
*A61F 2/28* (2006.01)
*A61L 27/36* (2006.01)
*A61L 27/46* (2006.01)
*A61F 2/46* (2006.01)

(52) U.S. Cl.
CPC ........... *A61L 27/3691* (2013.01); *A61L 27/365* (2013.01); *A61L 27/3608* (2013.01); *A61L 27/46* (2013.01); *A61F 2/28* (2013.01); *A61F 2/4644* (2013.01); *A61F 2002/2835* (2013.01); *A61F 2210/0004* (2013.01); *A61F 2210/0076* (2013.01); *A61F 2250/0067* (2013.01); *A61F 2310/00359* (2013.01); *A61F 2310/00371* (2013.01); *A61L 27/3687* (2013.01); *A61L 2400/06* (2013.01); *A61L 2430/02* (2013.01); *A61L 2430/40* (2013.01)

(58) Field of Classification Search
None
See application file for complete search history.

(56) References Cited

U.S. PATENT DOCUMENTS

| 5,573,771 | A * | 11/1996 | Geistlich et al. | 424/422 |
| 7,838,022 | B2 * | 11/2010 | Drapeau et al. | 424/423 |
| 2003/0039676 | A1 * | 2/2003 | Boyce et al. | 424/423 |
| 2005/0233454 | A1 * | 10/2005 | Nies et al. | 435/396 |
| 2006/0128948 | A1 * | 6/2006 | Taguchi et al. | 530/402 |
| 2008/0033572 | A1 * | 2/2008 | D'Antonio et al. | 623/23.51 |
| 2008/0140217 | A1 * | 6/2008 | Li et al. | 623/23.51 |

* cited by examiner

*Primary Examiner* — Thomas J Sweet
*Assistant Examiner* — Rebecca Preston
(74) *Attorney, Agent, or Firm* — Sorell Lenna & Schmidt LLP (57) ABSTRACT

A composition includes bone and collagen, wherein the collagen has been acid treated, and cross-linked via dehydrothermal treatment or by a cross-linking agent (e.g., a citric acid derivative) under a compressive force of at least approximately 40 MPa.

18 Claims, 1 Drawing Sheet

BONE/COLLAGEN COMPOSITES AND USES THEREOF

REFERENCE TO RELATED APPLICATIONS

This application is a national phase application of International Application No. PCT/US2008/086563, filed Dec. 12, 2008, which claims priority to U.S. Application No. 61/013,002, filed Dec. 12, 2007, the entire contents of both of which are incorporated herein by reference.

TECHNICAL FIELD

The invention relates to compositions including at least bone and collagen, methods of making the compositions, and methods of using the compositions in orthopedic and dental medicine.

BACKGROUND

Bone is a composite material composed of impure hydroxyapatite, collagen, and a variety of non-collagenous proteins, as well as embedded and adherent cells. Bone can be processed into an implantable biomaterial, such as an allograft, for example, by removing the cells, leaving behind the extracellular matrix. The processed bone material can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's bone or may alternatively be processed into soft, moldable, or flowable demineralized bone materials that have the ability to induce a cellular healing response.

The use of bone grafts and bone substitute materials in orthopedic medicine is well known. While bone wounds can regenerate without the formation of scar tissue, fractures and other orthopedic injuries take a long time to heal, during which the bone is unable to support physiologic loading. Metal pins, screws, and meshes are frequently required to replace the mechanical function of injured bone. However, metal is significantly stiffer than bone. Use of metal implants may result in decreased bone density around the implant site due to stress shielding. Furthermore, most metal implants are permanent and unable to participate in physiological remodeling.

Bone's cellular healing processes, using bone tissue formation by osteoblast cells coordinated with bone and graft resorption by osteoclast cells, permit bone grafts and certain bone substitute materials to remodel into endogenous bone that is almost indistinguishable from the original. However, the use of bone grafts is limited by the available shape and size of grafts and the desire to optimize both mechanical strength and degradation rate. Variations in bone size and shape among patients (and donors) also make bone grafts a less optimal substitute material. Bone substitute materials and bone chips are quickly remodeled but cannot immediately provide mechanical support.

SUMMARY

The invention relates to compositions including at least bone and collagen, methods of making the compositions, and methods of using the compositions in orthopedic and dental applications.

In one aspect, the invention features a composition including bone; and collagen, wherein the collagen is acid treated, and cross-linked via dehydrothermal treatment under a compressive force of at least approximately 40 MPa.

Embodiments may include one or more of the following features. The dehydrothermal treatment is not performed under vacuum. The dehydrothermal treatment is performed under a compressive force ranging from approximately 40 MPa to approximately 275 MPa. The dehydrothermal treatment at a temperature ranging from approximately 80° C. to approximately 120° C., e.g., from approximately 80° C. to approximately 90° C. The visible band structure of the collagen is preserved. The collagen includes mammalian collagen, e.g., bovine, human, or porcine collagen. The composition includes approximately 10% to approximately 50% by weight of collagen, e.g., approximately 20% to approximately 40% by weight of collagen, or approximately 30% by weight of collagen. The composition includes approximately 50% to approximately 90% by weight of bone, e.g., approximately 60% to approximately 80% by weight of bone, or approximately 70% by weight of bone. The composition further includes hydroxyapatite. The composition further includes an inorganic bone substitute material (e.g., calcium phosphate).

In another aspect, the invention features a composition including bone; and collagen, wherein the collagen is cross-linked using a chemical cross-linking agent (e.g., a citric acid derivative).

Embodiments may include one or more of the following features. The citric acid derivative includes N-hydroxysuccinimide modified citric acid. The cross-linking agent is not formaldehyde or gluteraldehyde. The collagen is cross-linked under a compressive force of at least approximately 40 MPa, e.g., from approximately 40 MPa to approximately 275 MPa. The collagen is not cross-linked under vacuum. The visible band structure of the collagen is preserved. The collagen includes mammalian collagen, e.g., bovine, human, or porcine collagen. The composition includes approximately 10% to approximately 50% by weight of collagen, e.g., approximately 20% to approximately 40% by weight of collagen, or approximately 30% by weight of collagen. The composition includes approximately 50% to approximately 90% by weight of bone, e.g., approximately 60% to approximately 80% by weight of bone, or approximately 70% by weight of bone. The composition further includes hydroxyapatite. The composition further includes an inorganic bone substitute material (e.g., calcium phosphate).

In another aspect, the invention features a composition including bone particles and collagen, wherein the composition is prepared by adding bone particles to a dispersion of collagen at an acidic pH ranging from approximately 3 to approximately 6; applying a compressive force at least approximately 40 MPa to the composition; and cross-linking the collagen by dehydrothermal treatment with no vacuum.

Embodiments may include one or more of the following features. The compressive force ranges from approximately 40 MPa to approximately 275 MPa. The dehydrothermal treatment is performed at a temperature ranging from approximately 80° C. to approximately 120° C., e.g., from approximately 80° C. to approximately 90° C. The visible band structure of collagen is preserved. The collagen includes mammalian collagen, e.g., bovine, human, or porcine collagen. The composition includes approximately 10% to approximately 50% by weight of collagen, e.g., approximately 20% to approximately 40% by weight of collagen, or approximately 30% by weight of collagen. The composition includes approximately 50% to approximately 90% by weight of bone, e.g., approximately 60% to approximately 80% by weight of bone, or approximately 70% by weight of bone. The composition further includes hydroxyapatite. The composition further includes an inorganic bone substitute material (e.g., calcium phosphate).

In another aspect, the invention features a method including contacting (e.g., adding) bone particles to a dispersion of collagen at an acidic pH ranging from approximately 3 to approximately 6 to form a composition; applying a compressive force to the composition (e.g., of at least approximately 40 MPa); and cross-linking components of the composition (e.g., the collagen) with no vacuum.

Embodiments may include one or more of the following features. The compressive force ranges from approximately 40 MPa to approximately 275 MPa. The dehydrothermal treatment is performed at a temperature ranging from approximately 80° C. to approximately 120° C., e.g., from approximately 80° C. to approximately 90° C. The visible band structure of the collagen is preserved. The collagen includes mammalian collagen, e.g., bovine, human, or porcine collagen. The composition includes approximately 10% to approximately 50% by weight of collagen, e.g., approximately 20% to approximately 40% by weight of collagen, or approximately 30% by weight of collagen. The composition includes approximately 50% to approximately 90% by weight of bone, e.g., approximately 60% to approximately 80% by weight of bone, or approximately 70% by weight of bone. The composition further includes hydroxyapatite. The composition further includes an inorganic bone substitute material (e.g., calcium phosphate).

In another aspect, the invention features a method including contacting bone particles to a dispersion of collagen at an acidic pH ranging from approximately 3 to approximately 6 to form a composition; applying a compressive force to the composition of at least approximately 40 MPa; and cross-linking a component of the composition (e.g., the collagen) with a cross-lining agent (e.g., a citric acid derivative).

Embodiments may include one or more of the following features. The citric acid derivative includes N-hydroxysuccinimide modified citric acid. The compressive force ranges from approximately 40 MPa to approximately 275 MPa. The dehydrothermal treatment is performed at a temperature ranging from approximately 80° C. to approximately 120° C., e.g., from approximately 80° C. to approximately 90° C. The visible band structure of the collagen is preserved. The collagen includes mammalian collagen, e.g., bovine, human, or porcine collagen. The composition includes approximately 10% to approximately 50% by weight of collagen, e.g., approximately 20% to approximately 40% by weight of collagen, or approximately 30% by weight of collagen. The composition includes approximately 50% to approximately 90% by weight of bone, e.g., approximately 60% to approximately 80% by weight of bone, or approximately 70% by weight of bone. The composition further includes hydroxyapatite. The composition further includes an inorganic bone substitute material.

Embodiments may include one or more of the following features or advantages.

The compositions can allow and encourage direct boney in-growth and remodeling, which can improve patient outcome.

The compositions can be formed into a variety of shapes and sizes.

The composite can be porous as-prepared and/or the porosity of the composite can change (e.g., increase) over time to support in-growth of bone.

Other aspects, features and advantages will be apparent from the description of the following embodiments and from the claims.

DEFINITIONS

As used herein, "bioactive agent" is used to refer to compounds or entities that alter, promote, speed, prolong, inhibit, activate, or otherwise affect biological or chemical events in a subject (e.g., a human). For example, bioactive agents may include, but are not limited to osteogenic, osteoinductive, and osteoconductive agents, anti-HIV substances, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-Parkinson agents, anti-spasmodics and muscle contractants including channel blockers, miotics and anti-cholinergics, anti-glaucoma compounds, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotics, targeting agents, chemotactic factors, receptors, neurotransmitters, proteins, cell response modifiers, cells, peptides, polynucleotides, viruses, and vaccines. In certain embodiments, the bioactive agent is a drug. In certain embodiments, the bioactive agent is a small molecule.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formulary-20, published by the United States Pharmcopeial Convention, Inc., Rockville Md., 2001, and the "Pharmazeutische Wirkstoffe", edited by Von Keemann et al., Stuttgart/New York, 1987, all of which are incorporated herein by reference. Drugs for human use listed by the U.S. Food and Drug Administration (FDA) under 21 C.F.R. §§330.5, 331 through 361, and 440 through 460, and drugs for veterinary use listed by the FDA under 21 C.F.R. §§500 through 589, all of which are incorporated herein by reference, are also considered acceptable for use in accordance with the present invention.

As used herein, "biodegradable", "bioerodable", or "resorbable" materials are materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Biodegradable materials also include materials that are broken down within cells. Degradation may occur by hydrolysis, enzymatic processes, phagocytosis, or other processes.

The term "biocompatible", as used herein, is intended to describe materials that, upon administration in vivo, do not induce undesirable side effects. In some embodiments, the material does not induce irreversible, undesirable side effects. In certain embodiments, a material is biocompatible if it does not induce long term undesirable side effects. In certain embodiments, the risks and benefits of administering a material are weighed in order to determine whether a material is sufficiently biocompatible to be administered to a subject.

The term "biomolecules", as used herein, refers to classes of molecules (e.g., proteins, amino acids, peptides, polynucleotides, nucleotides, carbohydrates, sugars, lipids, nucleoproteins, glycoproteins, lipoproteins, steroids, natural products, etc.) that are commonly found or produced in cells, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active fragments or subunits. In some embodiments, the biomolecule is a growth factor, chemotactic factor, cytokine, extracellular matrix molecule, or a fragment or derivative thereof, for example, a cell attachment sequence such as a peptide containing the sequence, RGD.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2"-fluororibose, deoxyribose, and hexose). Carbohydrates may exist in many different forms, for example, conformers, cyclic forms, acyclic forms, stereoisomers, tautomers, anomers, and isomers.

The term "citric acid derivative" refers to a cross-linking agent that is based on citric acid. For example, preparation of the citric acid derivative can include citric acid as a reactant.

The term "composite" is used to refer to a unified combination of two or more distinct materials. The composite may be homogeneous or heterogeneous. For example, a composite may be a combination of bone-derived particles and collagen; or a combination of a bone substitute material and collagen. In certain embodiments, the composite has a particular orientation.

"Demineralized" is used to refer to bone (e.g., particles) that have been subjected to a process that causes a decrease in the original mineral content. As utilized herein, the phrase "superficially demineralized" as applied to bone particles refers to bone particles possessing at least about 90% by weight of their original inorganic mineral content. The phrase "partially demineralized" as applied to the bone particles refers to bone particles possessing from about 8% to about 90% by weight of their original inorganic mineral content, and the phrase "fully demineralized" as applied to the bone particles refers to bone particles possessing less than about 8% by weight, for example, less than about 1% by weight, of their original inorganic mineral content. The unmodified term "demineralized" as applied to the bone particles is intended to cover any one or combination of the foregoing types of demineralized bone particles.

"Deorganified", as herein applied to matrices, particles, etc., refers to bone or cartilage matrices, particles, etc., that were subjected to a process that removes at least part of their original organic content. In some embodiments, at least 1%, 10%, 20%, 30%, 40%, 50%, 60%, 70%, 80%, 90%, or 99% of the organic content of the starting material is removed. Deorganified bone from which substantially all the organic components have been removed is termed "anorganic."

The term "mineralized" refers to bone that has been subjected to a process that caused a decrease in their original organic content (e.g., de-fatting, de-greasing). Such a process can result in an increase in the relative inorganic mineral content of the bone. Mineralization may also refer to the mineralization of a matrix such as extracellular matrix or demineralized bone matrix. The mineralization process may take either in vivo or in vitro.

"Non-demineralized", as herein applied to bone or bone particles, refers to bone or bone-derived material (e.g., particles) that have not been subjected to a demineralization process (i.e., a procedure that totally or partially removes the original inorganic content of bone).

The term "osteoconductive", as used herein, refers to the ability of a substance or material to provide surfaces which are receptive to the growth of new bone.

The term "osteogenic" refers to the ability of a substance or material that can induce bone formation.

"Osteoinductive", as used herein, refers to the quality of being able to recruit cells (e.g., osteoblasts) from the host that have the potential to stimulate new bone formation. In general, osteoinductive materials are capable of inducing heterotopic ossification, that is, bone formation in extraskeletal soft tissues (e.g., muscle).

The term "osteoimplant" is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, and oral and maxillofacial surgical procedures such as the repair of simple and compound fractures and non-unions, external, and internal fixations, joint reconstructions such as arthrodesis, general arthroplasty, deficit filling, disectomy, laminectomy, anterior cerival and thoracic operations, spinal fusions, etc.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are exemplary polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thithymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as RNAi, siRNA, or shRNA.

As used herein, a "polypeptide", "peptide", or "protein" includes a string of at least three amino acids linked together by peptide bonds. The terms "polypeptide", "peptide", and "protein", may be used interchangeably. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide", as used herein, refer to any polymer or oligomer of carbohydrate residues. The polymer or oligomer may consist of anywhere from two to hundreds to thousands of sugar units or more. "Oligosaccharide" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose), and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "porogen" refers to a chemical compound that may be part of the inventive composite and upon implantation or prior to implantation diffuses, dissolves, and/or degrades to leave a pore in the osteoimplant composite. The porogen may be introduced into the composite during manufacture, during preparation of the composite (e.g., in the operating room), or after implantation. The porogen essentially reserves space in the composite while the composite is being molded but once the composite is implanted the porogen diffuses, dissolves, or degrades, thereby inducing porosity into the composite. In this way the porogen provides latent pores. In certain embodiments, the porogen may also be leached out of the composite before implantation. This resulting porosity of the implant generated during manufacture or after implantation (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogen can also be natural or synthetic polymers, oligomers, or monomers that are water soluble or degrade quickly under physiological conditions. Exemplary polymers include polyethylene glycol, poly(vinylpyrollidone), pullulan, poly(glycolide), poly(lactide), poly(lactide-co-glycolide), other polyesters, and starches.

The terms "porosity" and "void volume" are used herein interchangeably and refer to the average amount of non-solid space contained in a material (e.g., a composite of the present invention). Such space is considered void of volume even if it contains a substance that is liquid at ambient or physiological temperature, e.g., 0.5° C. to 50° C. The porosity or void volume of a composite can be defined as the ratio of the total volume of the pores (i.e., void volume) in the material to the overall volume of the composite. Porosity may in certain embodiments refer to "latent porosity" wherein pores are only formed upon diffusion, dissolution, or degradation of a material occupying the pores. The pores in such an instance may be formed after implantation.

As used herein, the term "remodeling" describes the process by which native bone, processed bone allograft, whole bone sections employed as grafts, and other bony tissues are replaced with new cell-containing host bone tissue by the action of osteoclasts and osteoblasts. Remodeling also describes the process by which non-bony native tissue and tissue grafts are removed and replaced with new, cell-containing tissue in vivo. Remodeling also describes how inorganic materials (e.g., calcium-phosphate materials, such as β-tricalcium phosphate) is replaced with living bone.

The term "shaped" as used to characterize a material (e.g., composite) or an osteoimplant refers to a material or osteoimplant of a determined or regular form or configuration in contrast to an indeterminate or vague form or configuration (as in the case of a lump or other solid matrix of special form). The material may be shaped into any shape, configuration, or size. Materials can be shaped as sheets, blocks, plates, disks, cones, pins, screws, tubes, teeth, bones, portions of bones, wedges, cylinders, threaded cylinders, and the like, as well as more complex geometric configurations.

As used herein, the term "small molecule" is used to refer to molecules, whether naturally-occurring or artificially created (e.g., via chemical synthesis), that have a relatively low molecular weight. Typically, small molecules have a molecular weight of less than about 2,500 g/mol, for example, less than 1000 g/mol. In certain embodiments, mall molecules are biologically active in that they produce a local or systemic effect in animals, such as mammals, e.g., humans. In certain preferred embodiments, the small molecule is a drug. In certain embodiments, though not necessarily, the drug is one that has already been deemed safe and effective for use by an appropriate governmental agency or body (e.g., the U.S. Food and Drug Administration).

As used herein, the term "transformation" describes the process by which a material is removed from an implant site and replaced by host tissue after implantation. Transformation may be accomplished by a combination of processes, including but not limited to remodeling, degradation, resorption, and tissue growth and/or formation. Removal of the material may be cell-mediated or accomplished through chemical processes, such as dissolution and hydrolysis.

The phrase "wet compressive strength," as utilized herein, refers to the compressive strength of the osteoimplant after the osteoimplant has been immersed in physiological saline (water containing 0.9 g NaCl/100 ml water) for a minimum of 12 hours. Compressive strength is a well-known measurement of mechanical strength and is measured using the procedure described herein.

DETAILED DESCRIPTION OF CERTAIN EMBODIMENTS

The bone substitute compositions described below include bone (e.g., bone particles), collagen, and in some embodiments, one or more additives (e.g., a biomolecule). As described below, bone particles can be held together by reconstituted collagen to form a hard, weight bearing composite (e.g., an osteoimplant) in which bone and collagen are chemically bonded. During use, the composite is capable of retaining its strength and weight bearing properties until it is replaced by new tissue.

Briefly, the compositions can be prepared by slowly neutralizing an acidic dispersion of collagen with bone, and subsequently cross-linking the collagen. Cross-linking can be performed using a dehydrothermal treatment in which the collagen and the bone are placed under pressure (e.g., greater than one atmosphere) and heat (e.g., greater than 25° C.). In other embodiments, cross-linking is performed by placing the collagen and the bone under pressure, and chemically cross-linking the collagen and bone (e.g., with a citric acid derivative).

Bone

The compositions can include any type of bone or bone-derived material (both called "bone" herein). In some embodiments, the bone employed in the preparation of the compositions are obtained from cortical, cancellous, and/or corticocancellous bone. The bone may be derived from any vertebrate. The bone may be of autogenous, allogenic, and/or xenogeneic origin. In certain embodiments, the bone is autogenous, that is, the bone is from the subject being treated. In other embodiments, the bone is allogenic (e.g., from donors). In some embodiments, the source of the bone is matched to the eventual recipient of the compositions (i.e., the donor and recipient are of the same species). For example, human bone is typically used in a human subject. In certain embodiments, the bone is obtained from cortical bone of allogenic origin. In certain embodiments, the bone is obtained from bone of xenogeneic origin. Porcine and bovine bone are examples of xenogeneic bone tissue that can be used individually or in combination as sources for the bone-derived material. Xenogenic bone tissue may be combined with allogenic or autogenous bone. More than one kind or type of bone can be used.

Particles of bone can be formed by any process known to break down bone into small pieces. Exemplary processes for forming such particles include milling whole bone to produce fibers, chipping whole bone, cutting whole bone, grinding whole bone, fracturing whole bone in liquid nitrogen, or otherwise disintegrating the bone. Particles can optionally be sieved to produce particles of a specific size range. The particles may be of any shape or size. Exemplary shapes include spheroidal, plates, shards, fibers, cuboidal, sheets, rods, oval, strings, elongated particles, wedges, discs, rectangular, polyhedral, etc. In some embodiments, the particles may be from about 10 microns to about 1000 microns in diameter or more. In some embodiments, the particles may be from about 20 microns to about 800 microns in diameter or more. In certain embodiments, the particles range in size from approximately 100 microns in diameter to approximately 500 microns in diameter. In certain embodiments, the particles range in size from approximately 300 microns in diameter to approximately 800 microns in diameter. The diameter can be greater than or equal to about 100 microns, about 200 microns, about 300 microns, about 400 microns, about 500 microns, about 600 microns, or about 700 microns; and/or less than or equal to about 800 microns, about 700 microns, about 600 microns, about 500 microns, about 400 microns, about 300 microns, or about 200 microns. As examples, the bone particles can be pin shaped, with tapered ends having an average diameter of from about 100 microns to about 500 microns. As for irregularly shaped particles, the recited dimension ranges may represent the length of the greatest or smallest dimension of the particle.

In certain embodiments, the particle size distribution of the particles that are used to form the compositions with respect to a mean value may be plus or minus, e.g., about 10% or less of the mean value, about 20% or less of the mean value, about 30% or less of the mean value, about 40% or less of the mean value, about 50% or less of the mean value, about 60% or less of the mean value, about 70% or less of the mean value, about 80% or less of the mean value, or about 90% or less of the mean value. In other embodiments, the particle size distribution of the particles that are used to form the compositions with respect to a median value may be plus or minus, e.g., about 10% or less of the median value, about 20% or less of the median value, about 30% or less of the median value, about 40% or less of the median value, about 50% or less of the median value, about 60% or less of the median value, about 70% or less of the median value, about 80% or less of the median value, or about 90% or less of the median value. In certain embodiments, at least about 60, about 70, or about 80 weight percent of the particles posses a median length of about 10 microns to about 1000 microns in their greatest dimension. In certain embodiments, at least about 60, about 70, or about 80 weight percent of the particles posses a median length of about 20 microns to about 800 microns in their greatest dimension. For particles that are fibers or other elongated particles, at least about 60 weight percent, at least about 70 weight percent, or at least about 80 weight percent of the particles possess a median length of from about 2 to about 200 mm, or from about 10 to about 100 mm, a median thickness of from about 0.05 to about 2 mm, for example, from about 0.2 to about 1 mm, and a median width of from about 1 mm to about 20 mm, for example, from about 2 to about 5 mm. The particles may possess a median length to median thickness ratio from at least about 5:1 up to about 500:1, for example, from at least about 50:1 up to about 500:1, or from about 50:1 up to about 100:1; and a median length to median width ratio of from about 10:1 to about 200:1 and, for example, from about 50:1 to about 100:1. In certain embodiments, the bone particles are short fibers having a cross-section of about 300 microns to about 100 microns and a length of about 1 mm to about 4 mm.

The processing of the bone to provide the particles may be adjusted to optimize for the desired size and/or distribution of the particles. The compositions can be made using bone of a single shape or of different shapes. The desired properties of the compositions (e.g., mechanical properties) may also be engineered by adjusting the weight percent, shapes, sizes, distribution, etc. of the bone or the additive(s).

The bone may be demineralized, non-demineralized, mineralized, or anorganic. In certain embodiments, the resulting bone is used "as is" in preparing the compositions. In other embodiments, the particles are defatted and disinfected. An exemplary defatting/disinfectant solution is an aqueous solution of ethanol. Other organic solvent may also be used in the defatting and disinfecting the bone. For example, methanol, isopropanol, butanol, DMF, DMSO, diethyl ether, hexanes, glyme, tetrahydrofuran, chloroform, methylene chloride, and carbon tetrachloride may be used. In certain embodiments, a non-halogenated solvent is used. The defatting/disinfectant solution may also include a detergent (e.g., an aqueous solution of a detergent). In certain embodiments, at least about 10 to about 40 percent by weight of water (i.e., about 60 to about 90 weight percent of defatting agent such as alcohol) is present in the defatting/disinfecting solution to provide lipid removal and disinfection within a short period of time. An exemplary concentration range of the defatting solution is from about 60 to about 85 weight percent alcohol, for example, about 70 weight percent alcohol.

In certain embodiments, the bone (e.g., particles) is demineralized. The bone can be demineralized in accordance with known and/or conventional procedures in order to reduce their inorganic mineral content. Some demineralization methods remove the inorganic mineral component of bone by employing acid solutions. Such methods are well known in the art, see for example, Reddi, et al., *Proc. Nat. Acad. Sci.*, 1972, 69:1601-1605, the contents of which are incorporated herein by reference. The strength of the acid solution, the shape and dimensions of the bone and the duration of the demineralization treatment will determine the extent of demineralization. Reference in this regard is made to Lewandrowski, et al., *J. Biomed. Mater. Res.*, 1996, 31:365-372 and U.S. Pat. No. 5,290,558, the contents of both of which are incorporated herein by reference.

In an exemplary defatting/disinfecting/demineralization procedure, the bone particles are subjected to a defatting/disinfecting step, followed by an acid demineralization step. An exemplary defatting/disinfectant solution is an aqueous solution of ethanol. In certain embodiments, at least about 10 to about 40 percent by weight of water (i.e., from about 60 to about 90 weight percent of defatting agent such as alcohol) is present in the defatting/disinfecting solution to provide lipid removal and disinfection. An exemplary concentration range of the defatting solution is from about 60 to about 85 weight percent alcohol, for example, about 70 weight percent alcohol. Ethanol can be the alcohol used in this step; however, other alcohols such as methanol, propanol, isopropanol, denatured ethanol, etc. may also be used. Following defatting, the bone is immersed in acid over time to effect their demineralization. The acid also disinfects the bone by killing viruses, vegetative microorganisms, and spores. Acids which can be employed in this step include inorganic acids such as hydrochloric acid and organic acids such as peracetic acid. After acid treatment, the demineralized bone is rinsed with sterile water to remove residual amounts of acid and thereby raise the pH. The bone may be dried, for example, by lyophilization, before being incorporated into the composite. The bone may be stored under aseptic conditions, for example, in a lyophilized state, until they are used or sterilized using known methods (e.g., gamma irradiation) shortly before being used.

As utilized herein, the phrase "superficially demineralized" as applied to the bone refers to bone particles possessing at least about 90% by weight of its original inorganic mineral content. The phrase "partially demineralized" as applied to the bone refers to bone possessing from about 8% to about 90% weight of its original inorganic mineral content, and the phrase "fully demineralized" as applied to the bone refers to bone possessing less than about 8%, for example, less than about 1%, by weight of its original inorganic mineral content. The unmodified term "demineralized" as applied to the bone is intended to cover any one or combination of the foregoing types of demineralized bone, that is, superficially demineralized, partially demineralized, or fully demineralized bone.

In an alternative embodiment, surfaces of bone may be lightly demineralized according to the procedures in our commonly owned U.S. Ser. No. 10/285,715, filed Nov. 1, 2002, published as U.S. Patent Publication No. 2003/0144743, on Jul. 31, 2003, the contents of which are incorporated herein by reference. Even minimal demineralization, for example, of less than 5% removal of the inorganic phase, increases the hydroxylation of bone and the surface concentration of amine groups. Demineralization may be so minimal, for example, less than 1%, that the removal of the calcium phosphate phase is almost undetectable. Rather, the enhanced surface concentration of reactive groups defines the extent of demineralization. This may be measured, for example, by titrating the reactive groups. In some embodiments, in a polymerization reaction that utilizes the exposed allograft surfaces to initiate a reaction, the amount of unreacted monomer remaining may be used to estimate reactivity of the surfaces. Surface reactivity may be assessed by a surrogate mechanical test, such as a peel test of a treated sample of bone adhering to a polymer.

In certain embodiments, the bone is subjected to a process that partially or totally removes their initial organic content to yield mineralized and anorganic bone particles, respectively. Different mineralization methods have been developed and are known in the art (Hurley et al., *Milit. Med.* 1957, 101-104; Kershaw, *Pharm. J.* 6:537, 1963; and U.S. Pat. No. 4,882,149; each of which is incorporated herein by reference). For example, a mineralization procedure can include a de-greasing step followed by a basic treatment (with ammonia or another amine) to degrade residual proteins and a water washing (U.S. Pat. Nos. 5,417,975 and 5,573,771; both of which are incorporated herein by reference). Another example of a mineralization procedure includes a defatting step where the bone is sonicated in 70% ethanol for 1-3 hours.

If desired, the bone can be modified in one or more ways, e.g., their protein content can be augmented or modified as described, for example, in U.S. Pat. Nos. 4,743,259 and 4,902,296, the contents of both of which are incorporated herein by reference.

Mixtures or combinations of one or more of the foregoing types of bone can be employed. For example, one or more of the foregoing types of demineralized bone can be employed in combination with non-demineralized bone, i.e., bone that have not been subjected to a demineralization process, or inorganic materials. The amount of each individual type of bone employed can vary widely depending on the mechanical and biological properties desired. Thus, mixtures of bone of various shapes, sizes, and/or degrees of demineralization may be assembled based on the desired mechanical, thermal, chemical, and biological properties of the composite. A desired balance between the various properties of the compositions (e.g., a balance between mechanical and biological properties) may be achieved by using different combinations of bone. Amounts of various bones can be readily determined by those skilled in the art on a case-by-case basis by routine experimentation.

The differential in strength, osteogenicity, and other properties between partially and fully demineralized bone on the one hand, and non-demineralized, superficially demineralized bone, inorganic ceramics, and bone substitutes on the other hand can be exploited. For example, in order to increase the compressive strength of the compositions, the ratio of nondemineralized and/or superficially demineralized bone to partially or fully demineralized bone may favor the former, and vice versa. The bone in the compositions also play a biological role. Non-demineralized bone brings about new bone in-growth by osteoconduction. Demineralized bone likewise play a biological role in bringing about new bone in-growth by osteoinduction. Both types of bone are gradually remodeled and replaced by new host bone over time. Thus, the use of various types of bone can be used to control the overall mechanical and biological properties, i.e., the strength, osteoconductivity, and/or osteoinductivity, etc., of the compositions.

Surface Modification of Bone

The bone may be optionally treated to enhance its interaction with the other components of the compositions (e.g., collagen) and/or to confer some property to the bone surface. Surface modification may provide a chemical substance that is strongly bonded to the surface of the bone, e.g., covalently bonded to the surface. The bone may also be coated with a material to facilitate interaction with the other components of the compositions.

For example, a biologically active compound such as a biomolecule, a small molecule, or a bioactive agent may be attached to the bone through a linker. As an example, mercaptosilanes can react with the sulfur atoms in proteins to attach them to the bone. Aminated, hydroxylated, and carboxylated silanes can react with a wide variety functional groups. The linker may be optimized for the compound being attached to the bone.

Biologically active molecules can modify non-mechanical properties of the compositions. For example, immobilization of a drug on the bone allows it to be gradually released at an implant site as the compositions are replaced by new tissue. Anti-inflammatory agents embedded within the compositions can control the inflammatory response long after the initial response to implantation of the compositions. Compounds may also be immobilized on the bone that are designed to elicit a particular metabolic response or to attract cells to the injection site.

Non-biologically active materials may also be attached to the bone. For example, radioopaque (e.g., barium sulfate), luminescent, or magnetically active particles may be attached to the bone using the techniques described above. If a material, for example, a metal atom or cluster, cannot be produced as a silane or other group that reacts with calcium phosphate ceramics, then a chelating agent may be immobilized on the bone surface and allowed to form a chelate with the atom or cluster. As the composition is replaced with new tissue, these non-biodegradable materials can be removed from the tissue site by natural metabolic processes, allowing the use of standard medical diagnostic techniques to track the compositions in vivo.

In an alternative embodiment, the bone surface is chemically treated before being modified. For example, non-demineralized bone-derived particles may be rinsed with phosphoric acid, e.g., for 1 to 15 minutes in a 5-50% solution by volume. Those skilled in the art will recognize that the relative volume of the bone and phosphoric acid solution (or any other solution used to treat the bone) may be optimized depending on the desired level of surface treatment. Agitation will also increase the uniformity of the treatment both along individual particles and across an entire sample of particles. The phosphoric acid solution reacts with the mineral component of the bone to coat the bone with calcium phosphate, which may increase the affinity of the surface for inorganic coupling agents. The surface may be partially demineralized to expose the collagen fibers at the bone surface.

Additionally or alternatively, the surface treatments described above or treatments such as etching may be used to increase the surface area or surface roughness of the bone. Such treatments can increase the interfacial strength at the bone interface by increasing the surface area of the interface. Such surface treatments may also be employed to round the shape or smooth the edges of the bone.

Bone Substitute Materials

Inorganic materials, including, but not limited to, calcium phosphate materials and other bone substitute materials, may also be exploited for use as particulate inclusions in the compositions. Exemplary inorganic materials include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, and BIOGLASS™, a calcium phosphate silica glass available from U.S. Biomaterials Corporation. Substituted calcium phosphate phases can also be used, including, but not limited to, fluorapatite, chlorapatite, magnesium-substituted tricalcium phosphate, and carbonate hydroxyapatite. In certain embodiments, the inorganic material is a substituted form of hydroxyapatite. For example, the hydroxyapatite may be substituted with other ions such as fluoride, chloride, magnesium, sodium, potassium, etc. Additional calcium phosphate phases suitable include those disclosed in U.S. Pat. RE 33,161 and RE 33,221 to Brown et al.; U.S. Pat. Nos. 4,880,610; 5,034,059; 5,047,031; 5,053,212; 5,129,905; 5,336,264; and 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., U.S. Pat. No. 5,650,176 to Lee et al., and 6,206,957 to Driessens et al, and biologically-derived or biomimetic materials such as those identified in Lowenstam H A, Weiner S, *On Biomineralization*, Oxford University Press, 1989; each of which is incorporated herein by reference.

Additives

Other additives to the compositions may be any type of chemical compound including proteins, peptides, polynucleotides (e.g., vectors, plasmids, cosmids, artificial chromosomes, etc.), lipids, carbohydrates, organic molecules, small molecules, organometallic compounds, metals, inorganic materials, polymers, etc. Living cells, tissue samples, or viruses may also be added to the compositions. In certain embodiments, the additional material includes cells, which may optionally be genetically engineered. For example, the cells may be engineered to produce a specific growth factor, chemotactic factor, osteogenic factor, etc. In certain embodiments, the cells may be engineered to produce a polynucleotide such as an siRNA, shRNA, RNAi, microRNA, etc. The cell may include a plasmid or other extra-chromosomal piece of DNA. In certain embodiments, a recombinant construct is integrated into the genome of the cell. In certain embodiments, the additives include a virus. Again, the virus may be genetically engineered. Tissues such as bone marrow and bone samples may be included in the compositions.

In certain embodiments, the compositions include a wetting or lubricating agent. Examples of wetting agents include water, organic protic solvents, aqueous solutions such as physiological saline, concentrated saline solutions, sugar solutions, ionic solutions of any kind, and liquid polyhydroxy compounds such as glycerol, polyethylene glycol (PEG), polyvinyl alcohol (PVA), and glycerol esters, and mixtures of any of these. Biological fluids may also be used as wetting or lubricating agents. Examples of biological fluids include blood, lymph, plasma, serum, or marrow. Lubricating agents may include, for example, polyethylene glycol.

The compositions may be porous (e.g., after manufacture) or may become porous after implantation. For a general discussion of the use of porosity in osteoimplants, see U.S. patent application US 2005/0251267, published Nov. 10, 2005; which is incorporated herein by reference. A porous composite osteoimplant with an interconnecting network of pores has been shown to facilitate the invasion of cells and promote the organized growth of incoming cells and tissue (e.g., living bone). Allcock et al. "Synthesis of poly[(amino acid alkyl ester) phosphazenes" *Macromolecules* 10:824-830, 1977; Allcock et al. "Hydrolysis pathways for aminophosphazenes" *Inorg. Chem.* 21:515-521, 1982; Mikos et al. "Prevascularization of biodegradable polymer scaffolds for hepatocyte transplantation" *Proc. ACS Div. of Polymer Mater.* 66:33, 1992; Eggli et al. "Porous hydroxyapatite and tricalcium phosphate cylinders with two different pore size ranges implanted in the cancellous bone of rabbits" *Clin. Orthop.* 232:127-138, 1987; each of which is incorporated herein by reference. Porosity has also been shown to influence the biocompatibility and bony integration of some composites. White et al. "Biomaterial aspects of Interpore 200 porous hydroxyapatite" *Dental Clinical of N. Amer.* 30:49-67, 1986; which is incorporated herein by reference.

The porosity of the compositions may include both open and closed cells. The terms "open cells" and "open-celled structure" are used herein interchangeably and refer to a porous material with very large permeability, and where no significant surface barriers exist between cells (i.e., where the pores are connected). The terms "closed cells" and "close-celled structure" are used herein interchangeably and refer to a porous material where the pores are not connected, resulting in a weakly permeable material. Open cells can increase the paths for tissue to infiltrate the composite and can decrease degradation times. The proportion and size distribution ranges of open and closed cells of the compositions (e.g., before or after implantation) may be adjusted by controlling such factors as the identity of the porogen, percentage of porogen, percentage of bone, etc.

The compositions can exhibit high degrees of porosity over a wide range of effective pore sizes. Thus, the compositions may have, at once, macroporosity, mesoporosity and microporosity. Macroporosity is characterized by pore diameters greater than about 100 microns. Mesoporosity is characterized by pore diameters between about 100 microns about 10 microns; and microporosity occurs when pores have diameters below about 10 microns. In some embodiments, the compositions have a porosity of at least about 30%. For example, in certain embodiments, the compositions have a porosity of more than about 40%, more than about 50%, more than about 60%, more than about 70%, more than bout 80%, or more than about 90%. Advantages of a porous composition over less porous or non-porous composition include, but are not limited to, more extensive cellular and tissue in-growth into the composition, more continuous supply of nutrients, more thorough infiltration of therapeutics, and enhanced revascularization, allowing bone growth and repair to take place more efficiently. Furthermore, in certain embodiments, the porosity of the compositions may be used to load the compositions with biologically active agents such as drugs, small molecules, cells, peptides, polynucleotides, growth factors, osteogenic factors, etc, for delivery at the implant site.

In certain embodiments, the pores of the compositions are over 100 microns wide for the invasion of cells and bony in-growth. Klaitwatter et al. "Application of porous ceramics for the attachment of load bearing orthopedic applications" *J. Biomed. Mater. Res. Symp.* 2:161, 1971; each of which is incorporated herein by reference. In certain embodiments, the pore size ranges from approximately 50 microns to approximately 500 microns, for example, from approximately 100 microns to approximately 250 microns.

The porosity of the compositions may be accomplished using any means known in the art. Exemplary methods of creating porosity in a composition include, but are not limited to, particular leaching processes, gas foaming processing, supercritical carbon dioxide processing, sintering, phase transformation, freeze-drying, cross-linking, molding, porogen melting, polymerization, melt-blowing, and salt fusion (Murphy et al. *Tissue Engineering* 8(1):43-52, 2002; incorporated herein by reference). For a review, see Karageorgiou et al., *Biomaterials* 26:5474-5491, 2005; incorporated herein by reference. The porosity may be a feature of the compositions during manufacture or before implantation, or the porosity may only be available after implantation. For example, an implanted composition may include latent pores. These latent pores may arise from including porogens in the compositions.

The porogen may be any chemical compound that will reserve a space within the compositions and will diffuse, dissolve, and/or degrade prior to or after implantation leaving a pore in the compositions. Porogens can have the property of not being appreciably changed in shape and/or size during the procedure to make the compositions.

Porogens may be of any shape or size. The porogen may be spheroidal, cuboidal, rectangular, elonganted, tubular, fibrous, disc-shaped, platelet-shaped, polygonal, etc. In certain embodiments, the porogen is granular with a diameter ranging from approximately 100 microns to approximately 800 microns. In certain embodiments, the porogen is elongated, tubular, or fibrous. Such porogens provide increased connectivity of the pores of the compositions and/or also allow for a lesser percentage of the porogen in the compositions. The amount of the porogen may vary in the composite from about 1% to about 80% by weight. In certain embodiments, the porogen makes up from about 5% to about 80% by weight of the compositions. In certain embodiments, the porogen makes up from about 10% to about 50% by weight of the compositions. Pores in the compositions can improve the osteoinductivity or osteoconductivity of the compositions by providing holes for cells such as osteoblasts, osteoclasts, fibroblasts, cells of the osteoblast lineage, stem cells, etc. The pores provide the compositions with biological in growth capacity. Pores in the compositions may also provide for easier replacement of the compositions as bone is formed and/or remodeled. In some embodiments, the porogen is biocompatible.

The porogen may be a gas, liquid, or solid. Exemplary gases that may act as porogens include carbon dioxide, nitrogen, argon, or air. Exemplary liquids include water, organic solvents, or biological fluids (e.g., blood, lymph, plasma). The gaseous or liquid porogen may diffuse out of the osteoimplant before or after implantation thereby providing pores for biological in-growth. Solid porogens may be crystalline or amorphous. Examples of solid porogens include water soluble compounds. In certain embodiments, the water soluble compound has a solubility of greater than about 10 g per 100 mL water at 25° C. In certain embodiments, the water soluble compound has a solubility of greater than about 25 g per 100 mL water at 25° C. In certain embodiments, the water soluble compound has a solubility of greater than about 50 g per 100 mL water at 25° C. In certain embodiments, the water soluble compound has a solubility of greater than about 75 g per 100 mL water at 25° C. In certain embodiments, the water soluble compound has a solubility of greater than about 100 g per 100 mL water at 25° C. Examples of porogens include carbohydrates (e.g., sorbitol, dextran (poly(dextrose)), starch), salts, sugar alcohols, natural polymers, synthetic polymers, and small molecules (e.g., those that include pharmaceutical agents).

In certain embodiments, carbohydrates are used as porogens in the compositions. The carbohydrate may be a monosaccharide, disaccharide, or polysaccharide. The carbohydrate may be a natural or synthetic carbohydrate. In certain embodiments, the carbohydrate is a biocompatible, biodegradable carbohydrate. In certain embodiments, the carbohydrate is a polysaccharide. Exemplary polysaccharides include cellulose, starch, amylose, dextran, poly(dextrose), glycogen, etc. In certain embodiments, the polysaccharide is dextran. Very high molecular weight dextran has been found particularly useful as a porogen. For example, the molecular weight of the dextran may range from about 500,000 g/mol to about 10,000,000 g/mol, for example, from about 1,000,000 g/mol to about 3,000,000 g/mol. In certain embodiments, the dextran has a molecular weight of approximately 2,000,000 g/mol. Dextrans with a molecular weight higher than 10,000,000 g/mol may also be used as porogens. Dextran may be used in any form (e.g., particles, granules, fibers, elongated fibers) as a porogen. In certain embodiments, fibers or elongated fibers of dextran are used as the porogen. Fibers of dextran may be formed using any known method including extrusion and precipitation. Fibers may be prepared by precipitation by adding an aqueous solution of dextran (e.g., about 5-25% dextran) to a less polar solvent such as a 90-100% alcohol (e.g., ethanol) solution. The dextran precipitates out in fibers that can be particularly useful as porogens. Dextran may be about 15% by weight to about 30% by weight of the compositions. In certain embodiments, dextran is about 15% by weight, 20% by weight, 25% by weight, or 30% by weight. Higher and lower percentages of dextran may also be used. Once the compositions with the dextran as a porogen are implanted into a subject, the dextran can dissolve away very quickly, leaving behind pores in the osteoimplant compositions. An advantage of using dextran in the compositions is that dextran can exhibit a hemostatic property in the extravascular space. Therefore, dextran in a composition can decrease bleeding at or near the site of implantation.

Examples of salts that can be used as porogens include lactate salts, such as calcium lactate and/or sodium lactate.

Polymers that are removed faster than the other components of the compositions can also be considered porogens. Examples of polymers that may be used as porogens include poly(vinyl pyrollidone), pullulan, poly(glycolide), poly(lactide), and poly(lactide-co-glycolide), or a derivative thereof. Typically low molecular weight polymers are used as porogens.

Alternatively or additionally, the compositions may contain one or more biologically active molecules, including biomolecules, small molecules, and bioactive agents, to promote bone growth and connective tissue regeneration, and/or to accelerate healing. Examples of materials that can be incorporated include chemotactic factors, angiogenic factors, bone cell inducers and stimulators, including the general class of cytokines such as the TGF-β superfamily of bone growth factors, the family of bone morphogenic proteins, osteoinductors, and/or bone marrow or bone forming precursor cells, isolated using standard techniques. Sources and amounts of such materials that can be included are known to those skilled in the art.

The compositions can also include different enzymes. Examples of enzymes or similar reagents are proteases or hydrolases with ester-hydrolyzing capabilities. Such enzymes include, but are not limited to, proteinase K, bromelaine, pronase E, cellulase, dextranase, elastase, plasmin streptokinase, trypsin, chymotrypsin, papain, chymopapain, collagenase, subtilisin, chlostridopeptidase A, ficin, carboxypeptidase A, pectinase, pectinesterase, an oxireductase, an oxidase, or the like. The inclusion of an appropriate amount of such a degradation enhancing agent can be used to regulate implant duration.

The compositions may, alternatively or additionally, be used to deliver other pharmaceutical agents. For example, biologically active agents include substances useful in preventing infection at the implant site, as for example, antiviral, antibacterial, antiparasitic, antifungal substances, and combinations thereof. Other agents include substances capable of acting as a stimulant, sedative, hypnotic analgesic, anticonvulsant, and the like. Other examples of pharmaceutical agents include, but are not limited to, drugs that act at synaptic and neuroeffector junctional sites, drugs that can act on the central nervous system, drugs that can modulate inflammatory responses, antibiotics, anti-cancer agents, immunomodulatory agents, drugs acting on the blood and/or the blood-forming organs, hormones, hormones antagonists, agents affecting calcification and bone turnover, vitamins, gene therapy agents (e.g., viral vectors, nucleic acid-bearing liposomes, DNA-protein conjugates, anti-sense agents), other agents such as targeting agents, etc. RNAi or other similar technologies may be used to reduce the production of various factors.

Examples of bioactive agents that can be delivered using the compositions include, but are not limited to, non-collagenous proteins such as osteopontin, osteonectin, bone sialo proteins, fibronectin, laminin, fibrinogen, vitronectin, trombospondin, proteoglycans, decorin, proteoglycans, beta-glycan, biglycan, aggrecan, veriscan, tanascin, matrix gla protein hyaluran, cells; amino acids; peptides; inorganic elements; inorganic compounds; organometallic compounds; cofactors for protein synthesis; cofactors for enzymes; vitamins; hormones; soluble and insoluble components of the immune system; soluble and insoluble receptors including truncated forms; soluble, insoluble, and cell surface bound ligands including truncated forms; chemokines, interleukines; antigens; bioactive compounds that are endocytozed; tissue or tissue fragments; endocrine tissue; enzymes such as collagenase, peptidases, oxidases, etc; polymeric cell scaffolds with parenchymal cells; angiogenic drugs, polymeric carriers containing bioactive agents; encapsulated bioactive agents; bioactive agents in time-release form; collagen lattices, antigenic agents; cytoskeletal agents; cartilage fragments; living cells such as chondrocytes, osteoblasts, osteoclasts, fibroclasts, bone marrow cells, mesenchymal stem cells, etc; tissue transplants; bioadhesives; bone morphogenic proteins (BMPs), transforming growth factors (TGF-β), insulin-like growth factor, platelet derived growth factor (PDGF); fibroblast growth factors (FGF), vascular endothelial growth factors (VEGF), epidermal growth factor (EGF), growth factor binding proteins, e.g., insulin-like growth factors; angiogenic agents; bone promoters; cytokines; interleukins; genetic material; genes encoding bone promoting action; cells containing genes encoding bone promoting action; cells genetically altered by the hand of man; externally expanded autograft or xenograft cells; growth hormones such as somatotropin; bone digestors; anti-tumor agents; fibronectin; cellular attractants and attachment agents; immunosuppressants; bone resorption inhibitors and stimulators; mitogenic factors; bioactive factors that inhibit and stimulate second messenger molecules; cell adhesion molecules, e.g., cell-matrix and cell-cell adhesion molecules; secondary messengers; monoclonal antibodies specific to cell surface determinants on mesenchymal stem cells; portions of monoclonal antibodies specific to cell surface determinants on mesenchymal stem cells; portions of monoclonal antibodies specific to cell surface determinants on mesenchymal stem cells; clotting factors; polynucleotides; and combinations thereof. The amount of bioactive agent included in the compositions can vary widely and will depend on such factors as the agent being delivered, the site of administration, the patient's physiological condition, etc. The optimum levels will be determined in a specific case based upon the intended use of the implant.

The biologically or non-biologically active substances may be added after formation of the compositions, for example using standard dip or spray application techniques followed by drying. Alternatively, the compositions can be treated with reagents that regenerate functional groups to which biologically or non-biologically active substances can be chemically or physically attached. In certain embodiments, a substance is attached to the compositions using a linker so that the substance is free to associate with its receptor or site of action in vivo. In other embodiments, the substance to be delivered is attached to an antibody, of fragments thereof, that recognizes the epitope found within the compositions. In addition, the surface of the compositions can be submitted to plasma etching or chemical oxidation to render the compositions more reactive and increase its affinity for the agent to be attached to it (see, for example, U.S. Pat. Nos. 6,033,582 and 6,119,028, each of which is incorporated herein by reference in its entirety).

These materials need not be covalently bonded to a component of the compositions. A material may be selectively distributed on or near the surface of the compositions using the layering techniques described above. Alternatively or in addition, biologically active components may be covalently linked to the bone before combination with the collagen. For example, silane coupling agents having amine, carboxyl, hydroxyl, or mercapto groups may be attached to the bone through a silane and then to reactive groups on a biomolecule, small molecule, or bioactive agent.

Preparing the Compositions

Briefly, preparation of the compositions includes slow neutralization of an acidic collagen dispersion by the bone (e.g., bone particles), followed by dehydrothermal (DHT) cross-linking under conditions of high pressure and heat.

The pressure prevents denaturation of the collagen during the DHT process. This is counter to conventional thinking where DHT is brought about by the accelerated removal of water by an applied vacuum, and collagen is prevent from denaturing by limiting temperatures until most of the water is removed. The high pressure DHT process can maintain the collagen molecular configuration that can result in stronger bonds, and also can promote collagen to mineral bonding that can further increase strength. Furthermore, in some embodiments, pressure sustained throughout the molding process (e.g., using an automated hydraulic process) can continuously maintain the desired compressive pressure at each stage of compression to compensate for any decrease in pressure with fluid loss. This process can directly establish particulate intimate contact, thereby enhancing effectiveness of the DHT process.

The collagen can be derived from any collagen bearing tissue from an animal. The collagen can be allogenic or xenogenic. The collagen can be from skin, tendon, fascia, ligament, trachea, organ collagen, etc. In certain embodiments, the collagen is human collagen or other mammalian collagen (e.g., porcine, bovine, or ovine).

The collagen can be made into a water-based dispersion by an acid treatment using techniques known to the art. As an example, a dispersion can include about 0.2 mL of lactic acid in 100 mL of distilled/de-ionized water with about 1.0 g of collagen (e.g., skin, tendon, fascia, ligament, etc). In some embodiments, an acidic dispersion contains from about 0.1 wt % to about 3 wt % collagen, for example, from about 1 wt % (1 g collagen/100 mL solution) and 2 wt % collagen. The collagen particles (e.g., fibers, strands) in the dispersion are capable of self assembly.

Collagen has the ability to self-assemble into fibers, and this self-assembly has a significant role in maintaining the structure and the mechanical function of a given tissue. Collagen self-assembly occurs at physiological pH where the assembled collagen fibers have identifiable quarter staggered configurations with alternating light and dark bands when observed under high magnifications. The regions where the collagen molecules overlap are the dark banding regions, while the staggered collagen molecules spanning from dark band to dark band are the light banding regions. Within the overlapping region, collagen molecules are bound together by native cross-links that are formed as part of fiber formation and overall molecule stabilization. Native cross-links alone are not the only element that is maintaining the stability of collagen molecules. Hydrogen bonding between these molecules can be facilitated by water that can also play a role in collagen self-assembly. Water may also continue to influence collagen stability after self-assembly on the micro- and macro-molecular level where water helps to maintain collagen molecular conformation and mechanical properties.

At lower pH, collagen can disassemble into smaller fibril subunits. This physical transformation is termed swelling in acidic solutions. Without being bound by any particular theory, it is believed that the mechanism is made possible by the charges on the collagen protein becoming positive, which causes the collagen fibers to repel each other and deaggregate into subunits because the attractive forces of the interaction between triple helices are eliminated, which can result in a dispersion of insoluble collagen that is homogenous, opalescent, and optically isotropic. In some embodiments, the dispersed collagen includes long fibers with diameters in the range of from about 0.05 µm to about 2.5 µm, and lengths from about 5 µm to about 100 µm. This process of deaggregation is reversible when the collagen dispersion is brought to physiological pH with evident collagen fiber assembly, e.g., if the acidity of the dispersion has been maintained above pH 3. As a result, in some embodiments, the pH of the collagen dispersion ranges from about 3 to about 6.5, for example, from about 3 to about 5, from about 3 to about 4.6, or about 4. As an example, about 0.2 mL of lactic acid in about 100 mL of water provides a pH from about 4 to about 5.

The methods of preparing the osteoimplant compositions involve using different collagen characteristics under different pH conditions to form the compositions. For example, bone particles that are added to the acidic collagen dispersion slowly neutralize the dispersion as surface minerals from the bone are dissolved. The gradual rise in pH allows collagen assembly to take place around the bone particles, which may have exposed collagen fibers on their surfaces as a result of the mineral dissolution.

The physical property of a mixture formed after combining the collagen dispersion and the bone particles can be described as having plasticity, where the plastic component of the collagen matrix contacts the bone particles to cement the components together to form colloidal bodies. A consequence of this process is that the bone particles are softened, for example, because of the high water content and the acidity of the collagen dispersion. The softer bone particles may provide a more intimate union of the bone particles and collagen, and/or better adjustment of the components under pressure, as described below. The interactions between the bone particles and the collagen include chemical interactions that assist and enhance the mechanical interactions between the bone particles and the collagen to enhance overall stability of the compositions. In some embodiments, making bone composites including ovine bone and collagen have shown that the ovine components behave differently from bovine components. For examples, ovine composites can have a glossy residue and discoloration that may be the result of lipids that are present in the ovine bone and are driven out during dehydrothermal cross-linking. An additional processing step including supercritical $CO_2$ can be used to reduce the fat content in the ovine bone and to make the ovine composites similar in appearance to bovine composites.

The concentration of the bone in the mixture can range from about 1 wt % to about 99 wt %, and the concentration of the collagen can range from about 1 wt % to about 99 wt %. The ratio of bone to collagen can range from about 99 wt %:1 wt % to about 1 wt %:99 wt %, for example, about 90 wt %:10 wt %, about 80 wt %:20 wt %, about 70 wt %:30 wt %, about 60 wt %:40 wt %, or about 50 wt %:50 wt %. After the bone (and any additive(s)) is added to the collagen dispersion, the mixture is vigorously mixed, e.g., for about one minute to about three minutes, at room temperature to form a loose composite. Typically, mixing is sufficient when there is a physical transformation that is visible to the naked eye. The components in the mixture are no longer separated, and there is a layer of clear water just above the loose composite that indicates the composite is sufficiently combined.

Next, the mixture is placed into a mold having a cavity shaped according to the shape of a desired final osteoimplant (e.g., wedge, spacer, block, sphere, disc, etc), and incremental pressure is applied to the mixture. This mixture of loose bone particles and collagen (with the abundant incorporation of water and air) can be highly viscoelastic and tend to resist rapid compression. Without being bound by any particular theory, it is believed that slow, stepwise increases in compressive force used to mold the mixture slowly force air and water out of the mixture and give the components sufficient time to rearrange in the confining space. As the compressive force increases, the space that is available for component movement decreases. The stepwise compression can also serve to organize the internal structure of the mixture in which the collagen eventually assumes a lateral packing perpendicular to the direction of the applied compressive force into uniform stratified layers. The layering may be uniformly visible throughout the compositions to the naked eye, which indicates that the compositions are anisotropic composites. Stepwise compression can also bring the bone and the collagen into closer proximity so that more mechanical and chemical bonding can take place while preparing for the cross-linking step that follows. In some embodiments, (1) a compressive force of about 6,700 psi (or about 45.58 MPa) is initially applied to the mixture for about 30 minutes, and (2) the compressive force is incrementally increased by about 6,700 psi and the mixture is held at each incremental increase for about 30 minutes, until about 40,200 psi (or about 273.47 MPa) of force is applied for about 30 minutes. The initial compressive force applied can be greater than or equal to about 40 MPa, about 45 MPa, about 50 MPa, about 55 MPa, about 60 MPa, about 65 MPa, about 70 MPa, about 80 MPa, about 90 MPa, or about 100 MPa. The final compressive force applied can be greater than or equal to about 50 MPa, about 60 MPa, about 70 MPa, about 80 MPa, about 90 MPa, about 100 MPa, about 150 MPa, about 200 MPa, or about 250 MPa. There can be one or more (e.g., two, three, four, five, six, seven, eight, nine, ten or more) incremental steps between the initial compressive force applied and the final compressive force applied. The time at each step(s) can be greater than or equal to about 10 minutes, about 20 minutes, about 30 minutes, about 40 minutes, or about 50 minutes; and/or less than or equal to about 60 minutes, about 50 minutes, about 40 minutes, about 30 minutes, or about 20 minutes.

After compression, the collagen, which is still under pressure, is cross-linked. In some embodiments, heat is applied to cross-link the collagen by dehydrothermal (DHT) cross-linking. Without being bound by theory, it is believed that the mechanism of DHT cross-linking in collagen is a condensation reaction either by esterification or by amide formation and usually through the hydroxyproline groups found on the collagen triple-helix. DHT cross-linking can also be accompanied by a visible change in the collagen physical organization due to dehydration. The characteristic quarter staggered conformation of collagen undergoes densification, especially in the light banding region. This densification of the light banding region may be due to the collapse of the molecules while forming cross-links because the water that is present in maintaining the structure is removed. Collagen can show signs of denaturation beginning at temperatures that are slightly above the normal physiological temperature when fully hydrated and the denaturation temperature can be heavily influenced by the native and synthetically induced cross-links. Collagen denaturation is believed to follow a specific sequence of events that begins at a "thermally labile domain" where the triple helix is unzipped due to the increase in thermal energy that then leads to unraveling of the collagen triple helix. This region is sometimes called the hydroxyproline-free region.

Furthermore, there are two kinds of water that coexist within the bone tissue: bulk water that occupies the pore spaces of the bone, and interstitial water that exists in the space between collagen and mineral crystals. This latter space is defined as collagen-apatite porosity with <100 Å pore dimensions. The bulk water can interact readily with the collagen molecules it surrounds, while the interstitial water molecules confined within the collagen-apatite spaces are held immobile, thereby serving as part of the structural component of the bone tissue. In forming the compositions, the bulk water facilitates the softening of the bone particles while allowing movement of the components in the compositions under compression.

Solid-state Nuclear Magnetic Resonance (NMR) studies have suggested some functions of interstitial water and bone mechanics that exist on the molecular level. The studies have suggested that the interstitial water layer may mechanically couple the mineral and collagen in bone and act as a shock absorbing component, supplementing the shock absorbing properties of the collagen found in the bone tissue. The water in the interstitial layer may allow movements between the mineral crystals to reduce the stress and deformation exerted on the mineral crystals while it acts as a sacrificial layer that offers additional protection for collagen from shear under uniaxial stress. This balancing function of the interstitial water layer occurs readily in fully hydrated bone tissue, but it can be easily depleted under dehydration. Furthermore, the NMR studies reveal that while under hydrated conditions, the interstitial water is bridging collagen to mineral in areas without direct collagen to mineral interaction. But with the removal of the interstitial water layer, the previously water-bridged mineral and collagen are free to associate and possibly form permanent bonds.

Based on this understanding, collagen subjected to DHT cross-linking can be better safe guarded from heat denaturation without the assistance of high vacuum when moisture is present if collagen molecular movement can be reduced. Using the high compressive pressures described above (e.g., using die clamps that apply high compression molding forces) during DHT cross-linking, collagen movement can be limited. In some embodiments, the mixture including bone and collagen, which is still under pressure, is heated up to about 80° C.-120° C. (e.g., 80° C.-90° C.) to effect cross-linking. The temperature can be greater than or equal to about 80° C., about 85° C., about 90° C., about 95° C., about 100° C., about 105° C., about 110° C., or about 115° C.; and/or less than or equal to about 120° C., about 115° C., about 110° C., about 105° C., about 100° C., about 95° C., about 90° C., or about 85° C. The heating time can be greater than or equal to about 4 hours, about 5 hours, about 6 hours, or about 7 hours; and/or less than or equal to about 8 hours, about 7 hours, about 6 hours, or about 5 hours. In some embodiments, the mixture is heated over two hours from room temperature to about 87° C., and held at 87° C. for about 4-8 hours. At high temperatures, e.g., 120° C., the mixture should not be heated too long because it can produce a brittle final composition.

Other cross-linking techniques for medical applications can also be used (see, for example, U.S. Pat. No. 6,123,781, the contents of which are incorporated herein by reference) in preparing the bone/collagen compositions. For example, alternatively to cross-linking using heat, the collagen can be chemically cross-linked while under pressure. Examples of chemical cross-linking agents include citric acid, citric acid derivatives and modified citric acid derivatives, such as one prepared by modifying the three carboxyl groups of citric acid with N-hydroxysuccinimide (NHS) or another electrophile in the presence of 1-ethyl-3-(3-dimethyl aminopropyl) carbodiimide (EDC) hydrocholoride or another coupling agent (e.g., Taguchi et al., Materials Science and Engineering 2004; C 24: 775-780, 781-785, and 787-790; and Materials Science and Engineering C 2006; 26: 9-13). [

As other examples, compounds like 1-ethyl-3-(3-dimethylaminopropyl) carbodiimide (EDC) hydrochloride, either alone or in combination with N-hydroxysuccinimide (NHS) can crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, "Evaluation of collagen cross-linking techniques for the stabilization of tissue matrices," *Biotechnol. Appl. Biochem.,* 1993, 17:23-29; PCT Publication WO98/19718, the contents of both of which are incorporated herein by reference). Alternatively, hydroxymethyl phosphine groups on collagen may be reacted with the primary and secondary amines on neighboring chains (see U.S. Pat. No. 5,948,386, the entire contents of which are incorporated herein by reference). Standard cross-linking agents such as mono- and dialdehydes, polyepoxy compounds, tanning agents including polyvalent metallic oxides, organic tannins, and other plant derived phenolic oxides, chemicals for esterification or carboxyl groups followed by reaction with hydrazide to form activated acyl azide groups, dicyclohexyl carbodiimide and its derivatives and other heterobifunctional crosslinking agents, hexamethylene diisocyanate, and sugars may also be used to cross-link the collagen. In some embodiments, the cross-linking agent is substantially free of aldehyde and/or glutaldehyde. Additional cross-linking methods include irradiation, enzymatic treatment, etc.

The resulting, cross-linked bone/collagen composition is a hard osteoimplant capable of bearing a load. The osteoimplant can have a wet strength of from about 7 MPa to about 52 MPa. The wet strength can be greater than or equal to about 7 MPa, about 10 MPa, about 15 MPa, about 20 MPa, about 25 MPa, about 30 MPa, about 35 MPa, about 40 MPa, about 45 MPa, or about 50 MPa; and/or less than or equal to about 52 MPa, about 50 MPa, about 45 MPa, about 40 MPa, about 35 MPa, about 30 MPa, about 25 MPa, about 20 MPa, about 15 MPa, or about 10 MPa. The osteoimplant can be sterilized (e.g., using gamma irradiation) using conventional techniques prior to use.

Use or Administration of the Compositions

The compositions may be administered to a subject in need thereof using any technique known in the art. The subject is typically a patient with a disorder or disease related to bone. In certain embodiments, the subject has a bony defect such as a fracture. The subject is typically a mammal although any animal with bones may benefit from treatment with the inventive composite. In certain embodiments, the subject is a vertebrate (e.g., mammals, reptiles, fish, birds, etc.). In certain embodiments, the subject is a human. In other embodiments, the subject is a domesticated animal such as a dog, cat, horse, etc. Any bone disease or disorder may be treated using the compositions including genetic diseases, congenital abnormalities, fractures, iatrogenic defects, bone cancer, bone metastases, inflammatory diseases (e.g. rheumatoid arthritis), autoimmune diseases, metabolic diseases, and degenerative bone disease (e.g., osteoarthritis). In certain embodiments, the osteoimplant compositions are formulated for the repair of a simple fracture, compound fracture, or non-union; as an external fixation device or internal fixation device; for joint reconstruction, arthrodesis, arthroplasty, or cup arthroplasty of the hip; for femoral or humeral head replacement; for femoral head surface replacement or total joint replacement; for repair of the vertebral column, spinal fusion or internal vertebral fixation; for discectomy; for laminectomy; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; for revision surgery; for revision surgery of a total joint arthroplasty; and for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones.

After implantation, the compositions typically stay at the site of implantation and is gradually resorbed by the body as bone forms in and around it. The compositions are typically engineered to provide the mechanical strength necessary for the implantation site. The compositions may be resorbed after approximately 1 month to approximately 6 years. The resorption rate will depend on the components in the compositions, the site of implantation, the patient, disease condition, etc. In certain embodiments, the compositions last from approximately 1 month to approximately 6 months. In other embodiments, the compositions last from approximately 6 months to approximately 1 year. In other embodiments, the compositions last for approximately 1-2 years. In other embodiments, the compositions last for approximately 2-3 years. In other embodiments, the compositions last for approximately 5 years.

The compositions can be used as bone void fillers either alone or in combination with one or more other conventional devices, for example, to fill the space between a device and bone. Examples of such devices include, but are not limited to, bone fixation plates (e.g., cranofacial, maxillofacial, orthopedic, skeletal, and the like); screws, tacks, clips, staples, nails, pins or rods, anchors (e.g., for suture, bone, and the like), scaffolds, scents, meshes (e.g., rigid, expandable, woven, knitted, weaved, etc), sponges, polymers, implants for cell encapsulation or tissue engineering, drug delivery (e.g., carriers, bone ingrowth induction catalysts such as bone morphogenic proteins, growth factors, peptides, antivirals, antibiotics, etc), monofilament or multifilament structures, sheets, coatings, membranes (e.g., porous, microporous, resorbable, etc), foams (e.g., open cell or close cell), screw augmentation, cranial, reconstruction, and/or combinations thereof.

The following Example is intended to illustrate certain particular embodiments of the invention but are not intended to limit its scope, which is defined by the claims.

EXAMPLES

A collagen dispersion 1 wt % was made by adding 1 g of purified bovine tendon collagen to a solution of 100 mL distilled water and 0.2 mL (85%) lactic acid. The tendon collagen was allowed to soak in the acidic solution for 30 minutes. The tendon collagen changed from solid, non-transparent fiber bundles to a semi-transparent, dispersed state after 30 minutes. The dispersed tendon collagen was poured into a blender and blended at a low speed for no more than 5 second bursts. The low speed blending was repeated several times until no visible fiber bundles can be observed. The dispersion was allowed to cool in a refrigerator for 10-15 minutes before repeating the blending two more times. When the blending was completed, the tendon collagen dispersion has a viscous consistency with no visible non-dispersed collagen. If non-dispersed collagen is observed, it can be removed physically from the dispersion.

After blending, the dispersion typically contains air bubbles trapped within the viscous dispersion. The dispersion was centrifuged at 4500 rpm for 5 minutes to remove trapped air from the dispersion. The dispersion was then ready for bone composite fabrication. Unused dispersion can be retained and stored in a −5° C. refrigerator to prolong shelf life.

To fabricate the bone composite, the collagen dispersion was at room temperature before fabrication. Using a syringe, 10 mL of collagen dispersion was added to 3 g of bone shards in a flask. The content in the flask was vigorously swirled until the two components were well incorporated. Good incorporation of the two components can be indicated by the appearance of a thin layer of water separating from the now combined components. The components at this point can be called a loose composite.

The loose composite is now ready for compression. The loose composite was quickly loaded into a die of desired shape and dimension without squeezing much of the water content out from the loose composite. Then the die was loaded into a die clamp and placed on the carver press. First, about 6,700 psi of pressure was applied to the loose composite, and this pressure was sustained for at least 30 minutes. An additional about 6,700 psi of pressure was added to the loose composite, and this pressure was sustained for at least 30 minutes. The incremental increases in pressure and sustain times were repeated until 40,200 psi of pressure was reached. Once the pressure reached 40,200 psi, the loose composite was kept at this pressure for a minimum of 18 hours. Before removing the die from the carver press, it was confirmed that the clamp securing the piston in the die was tight so that the clamp can continue to sustain the pressure before continuing to cross-linking.

Dehydrothermal (DHT) cross-linking: The DHT cross-linking was performed by loading the die into an oven. The initial temperature in the oven was room temperature. The oven temperature was then set to 87° C. The time when the oven temperature reached 87° C. was noted, and the die was allowed to be heated at the set temperature for at least 6-8 hours. After 6-8 hours, the die was removed from the oven, and the compressed and cross-linked bone composite was removed from the die.

Modified citric acid derivative (mCAD) cross-linking: A modified citric acid derivative (mCAD) cross-linker uses cross-linking chemistry of 1-ethyl-3-(3-demythylaminopropyl) carbodiimide hydrochloride (EDC) and N-hydroxysuccinimide (NHS) in addition with citric acid (CA) as a modifier to the cross-linking chemistry to increase the number of cross-linking bond sites. The formulation of the CAD was selected to better introduce the cross-linker into a dense composite. The formulation for the mCAD was 5.0 g of CA, 9.58 g of NHS, and 15.45 g EDC dissolved in 80 ml ethanol.

Cross-linking of the bone composite with mCAD was performed by immersing the composite completely in the mCAD cross-linking solution under vacuum. The vacuum pulled air out of the composite and drew the cross-linking solution into the pores of the composite. The composite was cross-linked for 16-24 hours under vacuum. After cross-linking, the composite was removed from the cross-linking solution and ready for residual cross-linker deactivation and removal.

The three cross-linker deactivation solutions included: 1) 14.2 g/L of $Na_2HPO_4$ in distilled water, 2) 58 g/L NaCl in distilled water, and 3) 116 g/L NaCl in distilled water. The mCAD cross-linked composite was immersed in the first cross-linker deactivation solution under vacuum. The deactivation was complete when all the air was pulled out of the composite. The subsequent deactivations with the other cross-linker solutions were performed in the same manner. The composite was then dried under vacuum at room temperature overnight.

Figure 1:
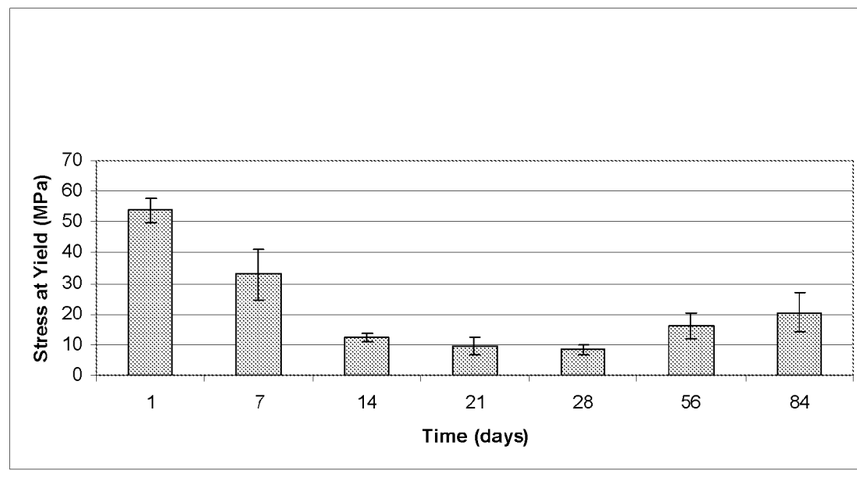
FIG. 1 is a graph of stress at yield (MPa) as a function of time from a bone/collagen composite.

Mechanical stability study: The compressive strength of the bone composites was tested over a period of about 3 months in vitro. The tests were conducted according to ASTM F-2077 or F-2267, but compressive forces were applied along and parallel to the longitudinal axis of t cylindrical samples. The compressive strength testing was performed with the bone composites positioned in the center of compressive platens with a preload of 10 N. The compression speed was set to 25 mm/min. The bone composites were compressed until failure. Referring to FIG. 1, the time points for each compressive strength testing in an Instron testing instrument were: 1 day, 7 days, 14 days, 21 days, 28 days, 56 days and 84 days. As shown, the stress at yield ranged from about 7 MPa to about 52 MPa.

Fatigue testing: Fatigue testing for the bone composites was used to understand the dynamic stability of the composites. Similar to the compressive strength testing above, the fatigue testing was performed in vitro. The composites were tested at 37° C. in a phosphate buffer solution (PBS). A 10% preload was applied to a composite before the start of a test. Different fatigue loads were applied to determine the optimal fatigue strength that the composite can withstand. As shown in Table 1 below, the fatigue load tested were 10%, 20%, 30%, and 40%. The conclusion of the fatigue test was set to 1 million cycles, or when the composite was compressed beyond a set mark of −2.0 mm from the initial height of the composite.

TABLE 1

| Fatigue load % | Number of fatigue cycles |
| --- | --- |
| 10% | >1 million cycles (test stopped) |
| 20% | >1 million cycles (test stopped) |
| 30% | Avg. 1.25 million cycles |
| 40% | Avg. 0.72 million cycles |

All references, such as patents, patent applications, and publications, referred to above are incorporated by reference in their entirety.

Other embodiments are within the scope of the following claims.

What is claimed is:

1. A composition comprising:
   approximately 10% to approximately 50% by weight of pressure treated collagen, wherein the pressure treated collagen is cross-linked using a citric acid derivative under a compressive force of at least approximately 40 MPa, and the composition is load bearing and has a wet compressive strength of from about 7 MPa to about 52 MPa;
   harvested bone including a linker configured to facilitate interactions with the pressure treated collagen; and
   the citric acid derivative.

2. The composition of claim 1, wherein the compressive force ranges from approximately 40 MPa to approximately 275 MPa.

3. The composition of claim 1, wherein a visible band structure of collagen fibers is preserved.

4. The composition of claim 1, wherein the pressure treated collagen comprises mammalian collagen.

5. The composition of claim 1, wherein the pressure treated collagen comprises bovine or porcine collagen.

6. The composition of claim 1, wherein the pressure treated collagen comprises human collagen.

7. The composition of claim 1, comprising approximately 20% to approximately 40% by weight of pressure treated collagen.

8. The composition of claim 1, comprising approximately 30% by weight of pressure treated collagen.

9. The composition of claim 1, comprising approximately 50% to approximately 90% by weight of harvested bone.

10. The composition of claim 1, comprising approximately 60% to approximately 80% by weight of harvested bone.

11. The composition of claim 1, comprising approximately 70% by weight of harvested bone.

12. The composition of claim 1, further comprising hydroxyapatite.

13. The composition of claim 1, further comprising an inorganic bone substitute material.

14. The composition of claim 1, wherein the citric acid derivative comprises N-hydroxysuccinimide modified citric acid.

15. The composition of claim 1, further comprising latent pores.

16. The composition of claim 15, wherein the latent pores comprise dextran and upon implantation of the composition to a surgical site the dextran dissolves leaving behind pores exhibiting a hemostatic property.

17. The composition of claim 1, wherein the harvested bone comprises bone shards having a particle size of about 10 microns to about 1000 microns.

18. A composition comprising bone particles and approximately 10% to approximately 50% by weight of pressure treated collagen, the bone particles comprising a linker configured to facilitate interactions with the pressure treated collagen, the composition being load bearing and having a wet compressive strength of from about 7 MPa to about 52 MPa, wherein the composition is prepared by adding bone particles to a dispersion of pressure treated collagen at an acidic pH ranging from approximately 3 to approximately 6;
   applying a compressive force at least approximately 40 MPa; and cross-linking the pressure treated collagen using a citric acid derivative, the composition further comprising the citric acid derivative.

* * * * *